(12) United States Patent
Chen et al.

(10) Patent No.: US 7,704,073 B2
(45) Date of Patent: Apr. 27, 2010

(54) ORTHODONTIC ARCHWIRES OF VARIOUS COLORS AND THEIR PREPARATION METHODS

(75) Inventors: Sinn-Wen Chen, Hsinchu (TW); Chiao-Ling Yang, Hsinchu (TW); Jee-Wei Emily Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 300 days.

(21) Appl. No.: 11/429,107

(22) Filed: May 8, 2006

(65) Prior Publication Data

US 2006/0199139 A1 Sep. 7, 2006

Related U.S. Application Data

(63) Continuation-in-part of application No. 10/810,800, filed on Mar. 29, 2004, now abandoned.

(51) Int. Cl.
*A61C 3/00* (2006.01)

(52) U.S. Cl. ......................................................... 433/20

(58) Field of Classification Search ................... 433/20
See application file for complete search history.

(56) References Cited

U.S. PATENT DOCUMENTS

| | | | |
|---|---|---|---|
| 3,075,896 A | 1/1963 | McGraw et al. | 205/224 |
| 3,346,469 A | 10/1967 | Weigel | 205/322 |
| 3,422,535 A | 1/1969 | Johnson | 433/218 |
| 3,616,279 A * | 10/1971 | Kendall | 205/211 |
| 3,834,024 A | 9/1974 | Kochavi | 433/207 |
| 4,252,620 A | 2/1981 | Tomita | 205/328 |
| 4,589,925 A | 5/1986 | Young | 134/3 |
| 4,722,689 A | 2/1988 | Corbett | 433/218 |
| 4,850,865 A * | 7/1989 | Napolitano | 433/8 |
| 5,160,599 A | 11/1992 | Kobayashi et al. | 205/106 |
| 5,382,347 A | 1/1995 | Yahalom | 205/50 |
| 5,685,987 A | 11/1997 | Hixon et al. | 210/636 |
| 5,816,801 A | 10/1998 | Farzin-Nia et al. | 433/8 |
| 6,036,489 A * | 3/2000 | Brosius | 433/20 |
| 6,095,809 A | 8/2000 | Kelly et al. | 433/20 |
| 6,164,964 A * | 12/2000 | Nakagawa | 433/9 |
| 6,254,383 B1 | 7/2001 | White | 433/18 |
| 6,406,295 B1 * | 6/2002 | Mahler | 433/173 |
| 2002/0168601 A1 | 11/2002 | Orikasa et al. | 433/9 |
| 2003/0059737 A1 * | 3/2003 | Hall | 433/25 |
| 2004/0076721 A1 | 4/2004 | Rosenfeld et al. | 426/87 |
| 2004/0117001 A1 * | 6/2004 | Pelton et al. | 623/1.15 |

FOREIGN PATENT DOCUMENTS

JP 02-115362 4/1990

* cited by examiner

*Primary Examiner*—Ralph A Lewis
(74) *Attorney, Agent, or Firm*—Bacon & Thomas, PLLC

(57) ABSTRACT

This invention provides orthodontic archwires with more than one colors, which can be prepared by subjecting the orthodontic archwires to an anodizing treatment.

21 Claims, 1 Drawing Sheet
(1 of 1 Drawing Sheet(s) Filed in Color)

ORTHODONTIC ARCHWIRES OF VARIOUS COLORS AND THEIR PREPARATION METHODS

CROSS-REFERENCE TO RELATED APPLICATION

The present application is a continuation-in-part application of U.S. patent application Ser. No. 10/810,800, filed Mar. 29, 2004. The above-listed application is commonly assigned with the present invention and the entire contents of which are incorporated herein by reference.

FIELD OF THE INVENTION

The present invention relates to metallic archwires with colors different from the original metallic gloss, and a method for preparing the metallic archwires. The invented method includes subjecting the metallic orthodontic archwires to an anodizing treatment or plasma treatment.

BACKGROUND OF THE INVENTION

Orthodontics has become a popular dental treatment where an orthodontic archwire is one of the main materials used in this treatment. At present, common orthodontic archwires used include stainless steel wires or β-Ti and Ni—Ti shape memory alloy wires. Andreasen uses a Ni—Ti alloy in orthodontic archwires [G. F. Andreasen, U.S. Pat. No. 4,037,324, (1977)], Burstone et al. are pioneers in using β-Ti material [C. J. Burstone and A. J. Goldberg, U.S. Pat. No. 4,197,643, (1980)]. Other ingredients are also introduced to form orthodontic archwires of various compositions [R. C. L. Sachdeva and F. Farzin, U.S. Pat. No. 5,683,245, (1997); K. Mitose and T. Ueki, U.S. Pat. No. 5,951,793, (1999); L. C. Schetky, M. H. Wu, C.-Y. Loi, and C. J. Burstone, U.S. Pat. No. 6,258,182, (2001); J. A. Davidson, A. K. Mishra, K. P. Daigle, and P. Kovacs, U.S. Pat. No. 5,573,401, (1996)]. Dental crowns are also commonly used for dental care. Metallic dental crowns are made either with noble metals or base metals, such as NiCr alloys.

The above-mentioned orthodontic archwires and metallic crowns all have bright metallic color. For cosmetic reasons, some orthodontic archwires are transparent, or even transparent with a nano structure. For example, Lemchen recently proposed a very different mesoporous alloidal orthodontic archwire [M. S. Lemchen, U.S. Pat. No. 6,056,545, (2000)]. The mesoporous alloidal orthodontic archwire invented by Lemchen has a transparency derived from the mesoporous nature thereof; it is expected that the mechanical strength thereof is inferior to the original dense material. This is a serious restriction on the use of orthodontic archwires.

U.S. Pat. No. 3,422,535 discloses a dental crown, which is anodized to provide an aesthetically pleasing color, such as gold.

US 2004/0117001 discloses anodizing archwires, among other medial implants, in order to provide a highly biocompatible surface, which resists corrosion.

US 2003/0059737 discloses a titanium oral device, which may be anodized in order to change its color.

U.S. Pat. No. 3,616,279 discloses a method for anodizing titanium and titanium alloys to provide a corrosion-resisting coating, which may vary in color depending on the applied voltage.

Japanese patent publication No. 02-115362 discloses a Ni—Ti shape memory alloy showing gold color, wherein nitrogen is ionized, accelerated and implanted into the surface of the Ni—Ti alloy, and the nitrogen-implanted Ni—Ti alloy is then heat-treated in vacuum or in an inert gas to form a compound layer of TiN showing an attractive gold color on the surface of the Ni—Ti alloy. The Ni—Ti alloy having gold color can be used as an orthodontic archwire.

Among the techniques available currently, there is no disclosure of a metallic orthodontic archwire having more than one colors on the surface thereof, and in particular by an anodizing treatment.

SUMMARY OF THE INVENTION

The present invention uses an anodizing treatment to treat metallic orthodontic archwires in order to increase the corrosion resistance thereof, while forming more than one colors thereon. The selection of a metallic material used in making the orthodontic archwires of the present invention is rather flexible—including a stainless steel wire with excellent properties, NiCr alloys and a shape memory alloy. Compared with the conventional orthodontic archwire, a product according to the present invention has no conspicuous difference in mechanical properties, while having more than one colors in meeting personal preferences.

BRIEF DESCRIPTION OF THE DRAWINGS

The patent application file contains at least one drawing executed in color. Copies of this patent application publication with color drawing(s) will be provided by the Office upon request and payment of the necessary fee.

DETAILED DESCRIPTION OF THE PREFERRED EMBODIMENTS

Figures 1A, 1B, 1C, 1D, 1E:
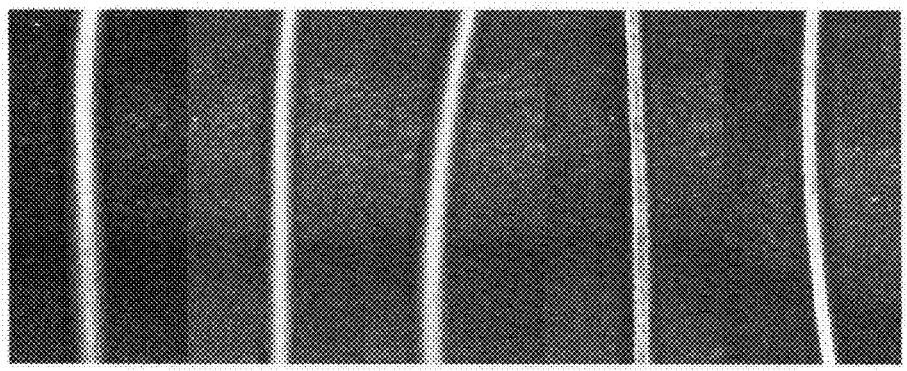
FIG. 1a is a photo showing an orthodontic archwire having more than one colors prepared in Example 11 of the present invention.
FIG. 1b is a photo showing an orthodontic archwire having more than one colors prepared in Example 12 of the present invention.
FIG. 1c is a photo showing an orthodontic archwire having more than one colors prepared in Example 13 of the present invention.
FIG. 1d is a photo showing an orthodontic archwire having more than one colors prepared in Example 14 of the present invention.
FIG. 1e is a photo showing an orthodontic archwire having more than one colors prepared in Example 15 of the present invention.

Preferred embodiments of the present invention include (but not limited to) the followings:

An orthodontic archwire having more than one color which are different from its original metallic gloss which is an orthodontic archwire wherein the colors of the orthodontic archwire are formed by an anodizing treatment at the same time and is made of an alloy mainly consisting of β-Ti, Ni, Ti and stainless steel and having two colors selected from blue, yellow, purple, green, golden, and tawny.

The orthodontic archwire having more than one color which are different from its original metallic gloss, which is an orthodontic archwire, wherein the colors of the orthodontic archwire are formed by an anodizing treatment at the same time, wherein the colors of said orthodontic archwire are three colors selected from blue, yellow, purple, green, golden, and tawny.

A method for preparing a colored orthodontic archwire, which comprises a) cleaning an orthodontic archwire; and b)

performing an anodizing treatment on the cleaned orthodontic archwire from step a) in order to obtain more than one colors on the surface of said orthodontic archwire different from its original metallic gloss, wherein an electrolytic solution used in said anodizing treatment is an acidic aqueous solution wherein an operation voltage of said anodizing treatment is 5 V-60 V, wherein said orthodontic archwire is made of an alloy mainly consisting of β-Ti, Ni and Ti and said electrolytic solution is an aqueous solution of a sulfate. The colors on the surface of said orthodontic archwire are two colors wherein the colors are selected from blue, yellow, purple, green, golden, and tawny.

The method for preparing a colored orthodontic archwire, which comprises a) cleaning an orthodontic archwire: and b) performing an anodizing treatment on the cleaned orthodontic archwire from step a) in order to obtain more than one colors on the surface of said orthodontic archwire different from its original metallic gloss, wherein an electrolytic solution used in said anodizing treatment is an acidic aqueous solution, wherein the colors on the surface of said orthodontic archwire are three colors selected from blue, yellow, purple, green, golden, and tawny.

The method for preparing a colored orthodontic archwire, which comprises a) cleaning an orthodontic archwire; and b) performing an anodizing treatment on the cleaned orthodontic archwire from step a) in order to obtain more than one colors on the surface of said orthodontic archwire different from its original metallic gloss, wherein an electrolytic solution used in said anodizing treatment is an acidic aqueous solution, wherein said cleaning comprises immersing said orthodontic archwire in an acidic aqueous solution, wherein an operation voltage of said anodizing treatment is 5 V-60 V, and said anodizing treatment in step b) is performed for a period of more than 30 minutes and for a period of about 120 minutes.

According to one of the preferred embodiments of the present invention, a metallic orthodontic archwire with more than one colors different from its original metallic gloss is provided.

The biocompatibility of an orthodontic archwire is very important because such an orthodontic archwire is mounted on the teeth of a person. Therefore, an ordinary dying or pigment coating technique can not be applied on the coloring of an orthodontic archwire. The coloring method of anodizing treatment according to the present invention uses the optical interference effect of the oxide film on the surface of the material without external addition of a pigment. The products resulting from the anodizing treatment are oxides of the metallic elements of the orthodontic archwire, which are formed on the surface of the orthodontic archwire. For an ordinary metal element, its oxide is often more stable than the metal element, that is the biocompatibility after anodizing treatment will become better. Therefore, the anodizing treatment will not introduce an additional biocompatibility problem. Furthermore, the anodizing treatment according to the present invention only oxidizes the surface of the material such that the mechanical strength of the orthodontic archwire will not be affected conspicuously. In other words, an anodizing treatment can alter the outlook color of an orthodontic archwire, without significantly changing the biocompatibility and mechanical strength thereof (wherein the former might be increased slightly, while the later might be decreased or increased slightly). The anodizing treatment of titanium metal has been widely elaborated in the literature (G. G. Turner, GB1100913, 1968; Shreir, GB962904, 1964; Kendull, U.S. Pat. No. 3,663,379, 1972; Kaminski, U.S. Pat. No. 6,029,390, 2000)—with a major emphasis on the titanium structural materials. Among the prior arts, there is completely no disclosure of anodizing treatment on the orthodontic archwires to obtain more than one colors on the surface thereof. The anodizing treatment is also applicable to dental crowns for altering the outlook color without significantly changing the biocompatibility and mechanical strength thereof.

Example 1

An orthodontic archwire of Ni—Ti alloy (code No. N-003, Ni—Ti orthodontic archwire from DCA Corp. of U.S.A.) was subjected to an anodizing treatment, wherein the electrolytic solution used was an aqueous solution prepared by dissolving 5 g of $Na_2SO_4.10H_2O$ in 400 ml of water, the anode was said orthodontic archwire, the cathode was a platinum plate, and the power supply was a LPS 305 from the MOTECH Co.

Said orthodontic archwire was immersed in a 0.5 M NaOH solution and subjected to an ultrasonic oscillation for 5 minutes. This alkaline washing treatment removed esters on the surface and activated the surface of the metal in order to achieve a uniform surface property. Next, said orthodontic archwire was immersed in a hydrochloric acid solution (30 g HCl/100 ml $H_2O$) and subjected to an ultrasonic oscillation for 10 minutes in order to remove the oxides on the metal surface, followed by washing with a large quantity of distilled water and drying by blowing. A constant voltage was used to perform an anodizing treatment at room temperature, wherein the voltage used was 10 V, and the anodizing treatment time was 120 minutes. Next, said orthodontic archwire was removed, washed with distilled water, and dried by blowing, to obtain a blue orthodontic archwire. Said orthodontic archwire has a bright metallic gloss of Ni—Ti alloy prior to receiving the treatment.

Example 2

An orthodontic archwire of Ni—Ti alloy (Code No. N-003, Ni—Ti orthodontic archwire from DCA Corp. of U.S.A.) was used as a specimen. The electrolytic solution used was an aqueous solution prepared by dissolving 10 g of $Na_2SO_4.10H_2O$ in 400 ml of water. The experiment system and method for pre-treating the specimen were identical to Example 1. The anodizing treatment was carried out at room temperature with a constant voltage. The operation voltage used was 10 V, and the anodizing treatment time was 120 minutes. Next, said specimen was removed, washed with distilled water, and dried by blowing, to obtain a yellow orthodontic archwire.

Example 3

An orthodontic archwire of Ni—Ti alloy (Code No. N-003, Ni—Ti orthodontic archwire from DCA Corp. of U.S.A.) was used as a specimen. The electrolytic solution used was an aqueous solution prepared by dissolving 20 g of $Na_2SO_4.10H_2O$ in 400 ml of water. The experiment system and method for pre-treating the specimen were identical to Example 1. The anodizing treatment was carried out at room temperature with a constant voltage. The operation voltage used was 10 V, and the anodizing treatment time was 120 minutes. Next, said specimen was removed, washed with distilled water, and dried by blowing, to obtain a purple orthodontic archwire.

Example 4

An orthodontic archwire of Ni—Ti alloy (Code No. N-003, NiTi orthodontic archwire from DCA Corp. of U.S.A.) was used as a specimen. The electrolytic solution used was an aqueous solution prepared by dissolving 5 g of $Na_2SO_4.10H_2O$ in 400 ml of water. The experiment system and method for pre-treating the specimen were identical to Example 1. The anodizing treatment was carried out at room temperature with a constant voltage. The operation voltage used was 20 V, and the anodizing treatment time was 120 minutes. Next, said specimen was removed, washed with distilled water, and dried by blowing, in order to obtain a blue orthodontic archwire.

Example 5

An orthodontic archwire of Ni—Ti alloy (Code No. N-003, NiTi orthodontic archwire from DCA Corp. of U.S.A.) was used as a specimen. The electrolytic solution used was an aqueous solution prepared by dissolving 10 g of $Na_2SO_4.10H_2O$ in 400 ml of water. The experiment system and method for pre-treating the specimen were identical to Example 1. The anodizing treatment was carried out at room temperature with a constant voltage. The operation voltage used was 20 V, and the anodizing treatment time was 120 minutes. Next, said specimen was removed, washed with distilled water, and dried by blowing, in order to obtain a green orthodontic archwire.

Example 6

A β-Ti orthodontic archwire (Code No. 100-942, β-Ti orthodontic archwire from INC Corp. of U.S.A.) was used as a specimen. The electrolytic solution used was an aqueous solution prepared by dissolving 10 g of $Na_2SO_4.10H_2O$ in 400 ml of water. The experiment system and method for pre-treating the specimen were identical to Example 1. The anodizing treatment was carried out at room temperature with a constant voltage. The operation voltage used was 60 V, and the anodizing treatment time was 5 minutes. Next, said specimen was removed, washed with distilled water, and dried by blowing, to obtain a purple orthodontic archwire.

Example 7

A β-Ti orthodontic archwire (Code No. 100-942, β-Ti orthodontic archwire from INC Corp. of U.S.A.) was used as a specimen. The electrolytic solution used was an aqueous solution prepared by dissolving 10 g of $Na_2SO_4.10H_2O$ in 400 ml of water. The experiment system and method for pre-treating the specimen were identical to Example 1. The anodizing treatment was carried out at room temperature with a constant voltage. The operation voltage used was 40 V, and the anodizing treatment time was 5 minutes. Next, said specimen was removed, washed with distilled water, and dried by blowing, to obtain a golden orthodontic archwire.

Example 8

A β-Ti orthodontic archwire (Code No. 100-942, β-Ti orthodontic archwire from INC of U.S.A.) was used as a specimen. The electrolytic solution used was an aqueous solution prepared by dissolving 10 g of $Na_2SO_4.10H_2O$ in 400 ml of water. The experiment system and method for pre-treating the specimen were identical to Example 1. The anodizing treatment was carried out at room temperature with a constant voltage. The operation voltage used was 20 V, and the anodizing treatment time was 5 minutes. Next, said specimen was removed, washed with distilled water, and dried by blowing, to obtain a blue orthodontic archwire.

Example 9

A β-Ti orthodontic archwire (Code No. 100-942, β-Ti orthodontic archwire from INC Corp. of U.S.A.) was used as a specimen. The electrolytic solution used was an aqueous solution prepared by dissolving 10 g of $Na_2SO_4.10H_2O$ in 400 ml of water. The experiment system and method for pre-treating the specimen were identical to Example 1. The anodizing treatment was carried out at room temperature with a constant voltage. The operation voltage used was 10 V, and the anodizing treatment time was 5 minutes. Next, said specimen was removed, washed with distilled water, and dried by blowing, to obtain a tawny orthodontic archwire.

Example 10

A NiCr dental crown was used as a specimen. The electrolytic solution used was an aqueous solution prepared by dissolving 5 g of $Na_2SO_4.10H_2O$ in 400 ml of water. The experiment system and method for pre-treating the specimen were identical to Example 1. The anodizing treatment was carried out at room temperature with a constant voltage. The operation voltage used was 5 V, and the anodizing treatment time was 30 minutes. Next, said specimen was removed, washed with distilled water, and dried by blowing, in order to obtain a slight bronze color.

Example 11

A Ni—Ti orthodontic archwire (Code No. N-003, Ni—Ti orthodontic archwire from DCA Corp. of U.S.A.) was used as a specimen. The electrolytic solution used was an aqueous solution prepared by dissolving 5 g of $Na_2SO_4.10H_2O$ in 150 ml of water. The experiment system and method for pre-treating the specimen were identical to Example 1. The anodizing treatment was carried out at 25° C. with a constant voltage. The operation voltage used was 20 V, and the anodizing treatment time was 120 minutes. Next, said specimen was removed, washed with distilled water, and dried by blowing, to obtain a slight purple shifting to slight yellow orthodontic archwire, as shown in FIG. 1a.

Example 12

A Ni—Ti orthodontic archwire (Code No. N-003, Ni—Ti orthodontic archwire from DCA Corp. of U.S.A.) was used as a specimen. The electrolytic solution used was an aqueous solution prepared by dissolving 5 g of $Na_2SO_4.10H_2O$ in 150 ml of water. The experiment system and method for pre-treating the specimen were identical to Example 1. The anodizing treatment was carried out at 25° C. with a constant voltage. The operation voltage used was 30 V, and the anodizing treatment time was 120 minutes. Next, said specimen was removed, washed with distilled water, and dried by blowing, to obtain a slight purple shifting to slight yellow and shifting to slight blue orthodontic archwire, as shown in FIG. 1b.

Example 13

A Ni—Ti orthodontic archwire (Code No. N-003, Ni—Ti orthodontic archwire from DCA Corp. of U.S.A.) was used as a specimen. The electrolytic solution used was an aqueous solution prepared by dissolving 5 g of $Na_2SO_4.10H_2O$ in 150 ml of water. The experiment system and method for pre-treating the specimen were identical to Example 1. The anodizing treatment was carried out at 25° C. with a constant voltage. The operation voltage used was 40 V, and the anodizing treatment time was 120 minutes. Next, said specimen was removed, washed with distilled water, and dried by blowing, to obtain a slight purple shifting to slight yellow and shifting slight blue orthodontic archwire, as shown in FIG. 1c.

Example 14

A Ni—Ti orthodontic archwire (Code No. N-003, Ni—Ti orthodontic archwire from DCA Corp. of U.S.A.) was used as a specimen. The electrolytic solution used was an aqueous solution prepared by dissolving 2.5 g of $Na_3PO_4 \cdot 10H_2O$ in 200 ml of water. The experiment system and method for pre-treating the specimen were identical to Example 1. The anodizing treatment was carried out at 25° C. with a constant voltage. The operation voltage used was 20 V, and the anodizing treatment time was 120 minutes. Next, said specimen was removed, washed with distilled water, and dried by blowing, to obtain a slight blue with discrete slight yellow spots orthodontic archwire, as shown in FIG. 1d.

Example 15

A Ni—Ti orthodontic archwire (Code No. N-003, Ni—Ti orthodontic archwire from DCA Corp. of U.S.A.) was used as a specimen. The electrolytic solution used was an aqueous solution prepared by dissolving 2.5 g of $Na_3PO_4 \cdot 10H_2O$ in 200 ml of water. The experiment system and method for pre-treating the specimen were identical to Example 1. The anodizing treatment was carried out at 25° C. with a constant voltage. The operation voltage used was 30 V, and the anodizing treatment time was 120 minutes. Next, said specimen was removed, washed with distilled water, and dried by blowing, to obtain a slight purple with discrete slight yellow spots orthodontic archwire, as shown in FIG. 1e.

The invention claimed is:

1. A metallic orthodontic archwire having an arched shape for engagement with orthodontic brackets positioned on an individual's teeth wherein said metallic orthodontic archwire is covered by an oxidized surface as a whole along a longitudinal direction of said archwire, said oxidized surface having a plurality of colors which are different from metallic gloss of the metallic orthodontic archwire before oxidation, wherein a first color of said archwire gradually shifts to a second color.

2. The orthodontic archwire as claimed in claim 1, wherein the colors of said orthodontic archwire are formed by an anodizing treatment.

3. The orthodontic archwire as claimed in claim 2, wherein said orthodontic archwire is made of an alloy mainly consisting of β-Ti.

4. The orthodontic archwire as claimed in claim 2, wherein said orthodontic archwire is made of an alloy mainly consisting of Ni and Ti.

5. The orthodontic archwire as claimed in claim 2, wherein said orthodontic archwire is made of an alloy mainly consisting of stainless steel.

6. The orthodontic archwire as claimed in claim 2, wherein the colors of said orthodontic archwire are two colors.

7. The orthodontic archwire as claimed in claim 6, wherein the colors are selected from blue, yellow, purple, green, golden, and tawny.

8. The orthodontic archwire as claimed in claim 2, wherein the colors of said orthodontic archwire are three colors.

9. The orthodontic archwire as claimed in claim 8, wherein the colors are selected from blue, yellow, purple, green, golden, and tawny.

10. A method for preparing a colored orthodontic archwire, which comprises the following steps:
    a) cleaning an arch shaped orthodontic archwire; and
    b) performing an anodizing treatment on the cleaned orthodontic archwire from step a) in order to obtain an oxidized surface along a longitudinal direction of said archwire as a whole having a plurality of colors on the surface of said orthodontic archwire different from metallic gloss of the metallic orthodontic archwire before oxidation, wherein a first color of said archwire gradually shifts to a second color and wherein an electrolytic solution used in said anodizing treatment is an acidic aqueous solution.

11. The method as claimed in claim 10, wherein an operation voltage of said anodizing treatment is 5 V-60 V.

12. The method as claimed in claim 11, wherein said anodizing treatment in step b) is performed for a period of more than 30 minutes.

13. The method as claimed in claim 11, wherein said anodizing treatment in step b) is performed for a period of about 120 minutes.

14. The method as claimed in claim 10, wherein said orthodontic archwire is made of an alloy mainly consisting of β-Ti, and said electrolytic solution is an aqueous solution of a sulfate.

15. The method as claimed in claim 10, wherein said orthodontic archwire is made of an alloy mainly consisting of Ni and Ti, and said electrolytic solution is an aqueous solution of a sulfate or phosphate.

16. The method as claimed in claim 10, wherein the colors on the surface of said orthodontic archwire are two colors.

17. The method as claimed in claim 16, wherein the colors are selected from blue, yellow, purple, green, golden, and tawny.

18. The method as claimed in claim 10, wherein the colors on the surface of said orthodontic archwire are three colors.

19. The method as claimed in claim 18, wherein the colors are selected from blue, yellow, purple, green, golden, and tawny.

20. The method as claimed in claim 10, wherein said cleaning comprises immersing said orthodontic archwire in an acidic aqueous solution.

21. A metallic orthodontic archwire having an arched shape for engagement with orthodontic brackets positioned on an individual's teeth wherein said metallic orthodontic archwire is covered by an oxidized surface as a whole along a longitudinal direction of said archwire, said oxidized surface having a plurality of colors which are different from metallic gloss of the metallic orthodontic archwire before oxidation, wherein a first color is formed as discrete spots on a second color.

* * * * *